United States Patent
Carniato et al.

(10) Patent No.: US 6,500,815 B1
(45) Date of Patent: Dec. 31, 2002

(54) SUBSTITUTED 11.BETA STEROID DERIVATIVES, METHOD FOR PREPARING SAME AND INTERMEDIATES OF SAID METHOD, USE AS MEDICINE AND COMPOSITIONS CONTAINING THEM

(75) Inventors: Denis Carniato, Cagnes-sur-Mer (FR); Thomas R. Gadek, Oakland, CA (US); Jochen Knolle, Frankfurt am Main (DE); Jean-Francois Gourvest, Claye-Souilly (FR); Anurschirwan Peyman, Kelkheim (DE); Sarah C. Bodary, San Bruno, CA (US)

(73) Assignees: Aventis Pharma S.A. (FR); Genentech, South San Francisco, CA (US)

( * ) Notice: Subject to any disclaimer, the term of this patent is extended or adjusted under 35 U.S.C. 154(b) by 0 days.

(21) Appl. No.: 09/914,025

(22) PCT Filed: Feb. 21, 2000

(86) PCT No.: PCT/FR00/00426

§ 371 (c)(1),
(2), (4) Date: Dec. 17, 2001

(87) PCT Pub. No.: WO00/50441

PCT Pub. Date: Aug. 31, 2000

(30) Foreign Application Priority Data

Feb. 22, 1999 (FR) ............................. 99 02152

(51) Int. Cl.[7] ........................ A61K 31/56; A61K 31/58; C07J 41/00; C07J 43/00

(52) U.S. Cl. .................. 514/176; 514/169; 514/172; 514/177; 540/107; 540/108; 552/516; 552/517; 552/518

(58) Field of Search .................. 514/169, 172, 514/176, 177; 552/516, 517, 518; 540/107, 108

(56) References Cited

FOREIGN PATENT DOCUMENTS

FR 0384842 8/1990

OTHER PUBLICATIONS

Marions et al, "The . . . Study", Mol. Hum. Reprod. (1998), vol. 4, No. 5, pp. 491–495.

Krishnakali et al, "Effects . . . Progesterone", Chemical Abstracts, vol. 114, No. 10, Mar. 1991, p. 429.

Volovel'skii et al, "Syntheses . . . Derivatives", Chemical Abstracts, vol. 92, No. 10, May 12, 1980, p. 623.

Shroff et al "Synthesis . . . Iminoprogestins", J. Med. Chem. (1971), vol. 14, No. 8, pp. 769–770.

*Primary Examiner*—Barbara P. Badio
(74) *Attorney, Agent, or Firm*—Bierman, Muserlian and Lucas

(57) ABSTRACT

The invention concerns compounds of formula (I) wherein: X, Y, $R_1$, $R_2$, Z, G are as defined in the description, the methods for preparing them and the intermediates in said method, their use as medicine and the pharmaceutical compositions containing them.

12 Claims, No Drawings

SUBSTITUTED 11.BETA STEROID DERIVATIVES, METHOD FOR PREPARING SAME AND INTERMEDIATES OF SAID METHOD, USE AS MEDICINE AND COMPOSITIONS CONTAINING THEM

This application is a 371 of PCT/FR00/00426 filed Feb. 21, 2000.

The present invention relates to new steroid derivatives, their preparation process and the intermediates of this process, their use as medicaments and the pharmaceutical compositions containing them.

A subject of the present invention is the compounds of general formula (I):

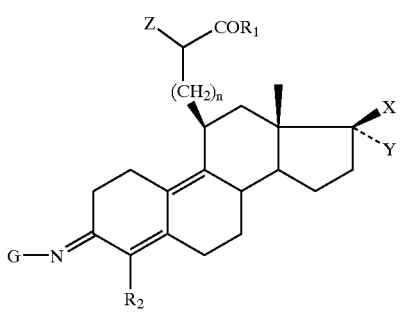

in which:
either X and Y form together with the carbon which carries them a C=O or C=CH$_2$ group,
or X represents a hydroxy, (C$_1$–C$_6$)-alkyloxy, (C$_1$–C$_6$)-alkylcarbonyloxy radical and Y is a hydrogen atom,
R$_1$ represents a hydroxy, (C$_1$–C$_6$)-alkyloxy, amino, (C$_1$–C$_6$)-alkylamino or (C$_2$–C$_{12}$)-dialkylamino radical,
R$_2$ represents a hydrogen or halogen atom,
Z represents a hydrogen atom, an NHSO$_2$Ra, NHCO$_2$Ra, NHCORa, NHSO$_2$NHRa or NHCONHRa group,
G represents:
either an N

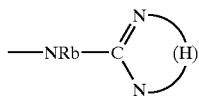

radical (G1 radical) in which (H) forms with the —N=C—NH— unit the remainder of a heterocycle,
or an NRbRc radical (G2 radical),
or a heterocycle (G3 radical),
or an NRb—C(=A)—NHRc radical (G4 radical) in which A is a sulphur, oxygen or NH atom,
or an NRb—SO$_2$Rc radical (G5 radical),
Ra, Rb and Rc, identical or different, represent a hydrogen atom, a —(CH$_2$)$_m$-Alk or —(CH$_2$)$_m$—Ar radical,
the term Alk representing a radical derived from a linear branched or cyclic, saturated or unsaturated, non-aromatic hydrocarbon, containing from 1 to 12 carbon atoms, substituted by R$_3$ or non-substituted, Ar representing a carbocyclic aryl substituted by R$_3$ or non-substituted,
n is an integer varying from 1 to 6, m represents 0, 1, 2 or 3,
the substituent R$_3$ represents:

halogen, oxo, cyano, nitro, formyl, carboxy, (C$_1$–C$_6$)-alkyloxycarbonyl, carboxamide,
an alkyl, alkenyl, alkynyl radical or containing from 1 to 6 atoms optionally substituted by one or more halogen atoms,
a cycloalkyl radical containing from 3 to 12 carbon atoms,
an alkoxy or alkylthio radical containing from 1 to 6 carbon atoms
an amino, alkylamino radical containing from 1 to 6 atoms carbon atoms,
an amino, alkylamino containing from 1 to 6 carbon atoms dialkylamino radical containing from 2 to 12 carbon atoms optionally in oxidized form,
an aminoalkyl containing from 1 to 6 carbon atoms or dialkylaminoalkyl radical containing from 3 to 8 carbon atoms,
a dialkylaminoalkyloxy radical containing from 3 to 18 carbon atoms,
an optionally acylated hydroxy radical containing from 1 to 12 carbon atoms,
an acyl radical containing from 1 to 12 carbon atoms optionally substituted for example by a chlorine, iodine or fluorine atom,
an aryl, carbocyclic or heterocyclic, aralkyl or aryloxy radical, these radicals being themselves optionally substituted by one or more substituents mentioned above,
said compounds of formula (I) being in all their possible isomer forms, isolated or in a mixture, as well as their esters and their addition salts with pharmaceutically acceptable acids and bases.

By the term Alk or alkyl containing from 1 to 12 carbon atoms, is designated in the case of acyclic hydrocarbons alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl pentyl, 3-ethylpentyl, n-octyl, 2,2-dimethylhexyl, 3,3-dimethylhexyl, 3-methyl-3-ethylpentyl, nonyl, 2,4-dimethylheptyl or n-decyl, alkenyl radicals such as vinyl, propenyl, isopropenyl, allyl, 2-methylallyl, butenyl or isobutenyl, or alkynyl radicals such as ethynyl, propynyl, propargyl, butylyl or isobutynyl, and in the case of cyclic radicals, cycloalkyl radicals, such as cyclopropyl, cyclobutyl, cyclopentyl, cyclohexyl or adamantyl radicals. Alkyl radicals containing from 1 to 6 carbon atoms and more particularly methyl, ethyl, propyl, isopropyl, butyl, isobutyl and tertbutyl are preferably meant.

By aryl, is meant a carbocyclic aryl group containing from 6 to 14 carbon atoms, is meant a radical derived from an aromatic cyclic hydrocarbon such as phenyl, naphthyl, phenanthrenyl radical or a radical derived from a condensed bicyclic or tricyclic hydrocarbon comprising a benzene ring such as indanyl, indenyl, dihydronaphthyl, tetrahydronaphthyl or fluorenyl. The junction occurs at the level of the benzene ring. It is preferably phenyl. By aralkyl, benzyl is preferably meant. By aryloxy phenyloxy is preferably meant.

By heterocycle, is meant an aromatic (heteroaryl) or non-aromatic heterocycle, saturated or non-saturated, comprising 1 to 9 carbon atoms and from 1 to 5 heteroatoms chosen from oxygen, nitrogen and sulphur atoms, the following are in particular designated:
heterocyclic monocyclic radicals, for example thienyl, furyl, pyranyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl radicals, heterocyclic condensed rings, for example benzofurannyl, benzothienyl, benzymidazolyl, benzothiazolyl, naphtho[2,3-b]thienyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also condensed polycyclic systems constituted by heterocyclic monocyclics as defined above such as for example furo[2,3-b]pyrrole or thieno[2,3-b]furan, or saturated heterocycles such as pyrrolidine, piperidine or morpholine.

When G is the G1 radical, G1 in particular represents one of the following heterocycles:

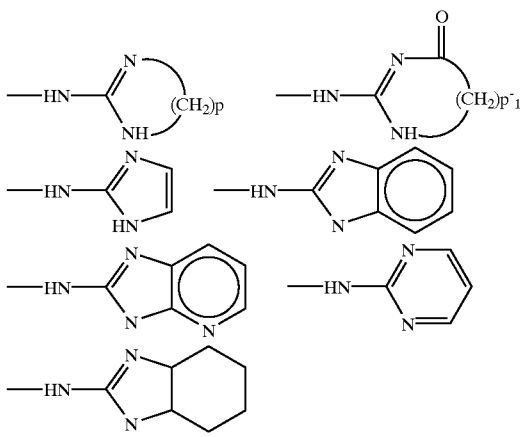

in which p represents an integer from 1 to 4 and preferably 2 or 3.

When G is the G2 radical, G2 can in particular be an amino, alkylamino such as —NHMe, —NHEt, dialkylamino such as —NMe$_2$, —NEt$_2$, —NMeEt, —NHPh, —NHCH$_2$Ph or —NHCH$_2$-pyrrol-2-yl group.

When G is the G4 or G5 radical, it is in particular the —NH—C(=NH)—NH$_2$, —NH—CO—NHCH$_2$Ph, —NHCONH$_2$, —NH—CS—NH$_2$, —NH—C(=NH)—NHCH$_2$Ph, —NH—C(=NH)—NHCH$_3$ or —NHSO$_2$Ph groups.

When R$_1$ represents alkyloxy or alkylamino it is in particular the following groups:

—OMe, —OEt, —O—(CH$_2$)$_2$—OH, —O—CH$_2$—CH(CH)—CH$_2$OH, —O—(CH$_2$)$_2$—NH$_2$, —O—(CH$_2$)$_2$—NMe$_2$ or —OCH$_2$Ph.

The optional R$_3$ substituents of the alkyl, aryl or heterocycle groups, as defined previously are chosen from the following radicals:

halogen: fluorine, chlorine, bromine, iodine, alkyl, alkenyl, alkynyl containing from 1 to 6 carbon atoms such as methyl, ethyl, propyl, isopropyl, butyl, isobutyl, tert-butyl, vinyl or allenyl. These radicals being themselves optionally substituted by one or more halogen atoms, for example fluorine such as trifluoromethyl, cycloalkyl containing from 3 to 12 carbon atoms such as cyclohexyl or adamantyl, oxo, cyano, nitro, formyl, carboxy and carboxyalkyl containing from 1 to 6 carbon atoms, carboxamide, alkoxy containing from 1 to 6 carbon atoms such as methoxy, ethoxy, propyloxy, isopropyloxy, butyloxy, alkylthio containing from 1 to 6 carbon atoms such as methylthio, ethylthio, propylthio, isopropylthio, butylthio, amino, alkylamino containing from 1 to 6 carbon atoms such as methylamino or ethylamino, dialkylamino containing from 2 to 12 carbon atoms such as dimethylamino, diethylamino, methylethylamino, each of these dialkylamino radicals being optionally in oxidized form, aminoalkyl containing from 1 to 6 carbon atoms such as aminomethyl or aminoethyl, dialkylaminoalkyl containing from 3 to 18 carbon atoms such as dimethylamino methyl or ethyl, dialkylaminoalkyloxy containing from 3 to 18 carbon atoms such as dimethylaminoethyloxy, optionally acylated hydroxyl containing from 1 to 12 carbon atoms, for example acetoxy, acyl containing from 1 to 12 carbon atoms such as formyl, acetyl, propionyl, butyryl, isobutyryl, valeryl, isovaleryl, succinyl, pivaloyl benzoyl optionally substituted for example by a chlorine, iodine or fluorine atom. The chloroacetyl, dichloroacetyl, trichloroacetyl, bromoacetyl or trifluoroacetyl radicals can be mentioned, carbocyclic or heterocyclic aryl such as phenyl, furyl, thienyl, pyridinyl, aralkyl such as benzyl, aryloxy such as phenyloxy, these radicals being themselves optionally substituted by the radicals mentioned above.

Of course, one or more R$_3$ substituents, identical or different, can be present. In the case of heterocycles, the substituents can be at the level of the carbon atom or the nitrogen atom.

The invention naturally extends to the salts of the compounds of formula (I), such as, for example, the salts formed when the compounds of formula (I) comprise an amino or amino guanidine function, with hydrochloric, hydrobromic, nitric, sulphuric, phosphoric, acetic, trifluoroacetic, formic, propionic, benzoic, maleic, succinic, tartaric, citric, oxalic, glyoxylic, aspartic, alkanesulphonic, such as methane or ethanesulphonic acids, arenesulphonic acids, such as benzene or paratoluene sulphonic and arylcarboxylic acids, or when the compounds of formula (I) comprise an acid function, with the salts of alkali or alkaline earth metals or optionally substituted ammonium.

In a first preferred group, a subject of the invention is the compounds of formula (I) as defined previously in which R$_1$ represents a hydroxyl and G is an NH—C(=NH)—NHRc radical as defined previously.

In a second preferred group, a subject of the invention is the compounds of formula (I) as defined previously in which R$_1$ represents a hydroxyl and G is chosen from the following heterocycles:

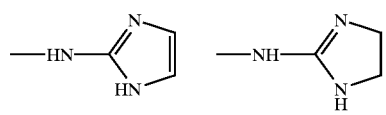

-continued

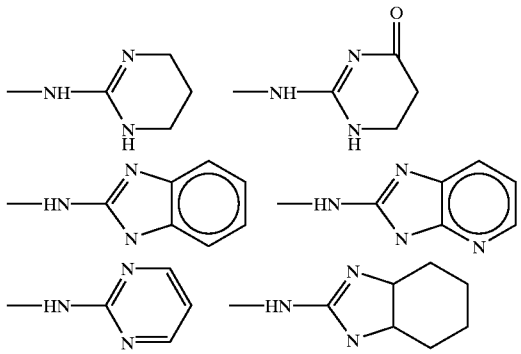

The invention also comprises all the tautomer forms of the compounds of formula (I) as defined above, for example relating to the form represented by formula (I) with G representing

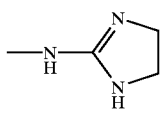

the following tautomer form:

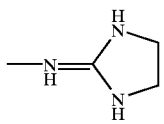

and all the other forms which differ by the different position of the hydrogen atom are considered.

In a third preferred group a subject of the invention is the compounds of formula (I) as defined previously in which Z is a hydrogen atom or an NHCO$_2$CH$_2$Ph, NHCOCH$_3$, NHCO$_2$CH$_2$-adamantyl group and G is an:

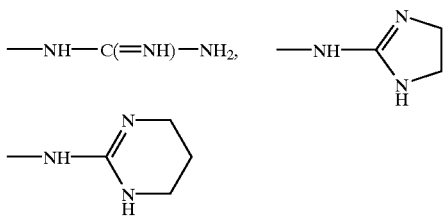

group.

In a fourth preferred group a subject of the invention is the following compounds:

ethyl-3-[(4,5-dihydro-1H-imidazol-2-yl)hydrazono]-17-oxo-.alpha.-[[(phenylmethoxy)carbonyl]amino]-estra-4,9-diene-11-beta-hexanoate, 3-[(4,5-dihydro-1H-imidazol-2-yl)hydrazono]-17-oxo-.alpha.-[[(phenylmethoxy)carbonyl]amino]-estra-4,9-diene-11-beta-hexanoic acid, 3-[(4,5-dihydro-1H-imidazol-2-yl)hydrazono]-17-hydroxy-.alpha.-[[(phenylmethoxy)carbonyl]amino]-estra-4,9-diene-11-beta-hexanoic acid, 3-[(aminoiminomethyl)hydrazono]-17-oxoestra-4,9-dien-11-beta-pentanoic acid, 3-[(1,4,5,6-tetrahydro-2-pyrimidinyl)hydrazono]-17-oxo-4,9-diene-11-beta-hexanoic acid, 3-[(4,5-dihydro-1H-imidazol-2-yl)hydrazono]-17-oxoestra-4,9-diene-11-beta-hexanoic acid, 4-chloro-3-[(4,5-dihydro-1H-imidazol-2-yl)hydrazono]-17-oxoestra-4,9-diene-11-beta-hexanoic acid, 3-[(aminoiminomethyl)hydrazono]-4-chloro-17-oxoestra-4,9-diene-11-beta-hexanoic acid.

3-[(aminoiminomethyl)hydrazono]-17-oxoestra-4,9-dien-11-beta-hexanoic acid,

6-[3-[(4,5-dihydro-1H-imidazol-2-yl)hydrazono]-17-methylene-estra-4,9-diene-11-beta-yl]-2-[[(phenylmethoxy)carbonyl]amino]-hexanoic acid.

The bone is constantly subjected to a dynamic process which includes bone resorption and bone formation. These processes are mediated via specialised cells. Bone formation is the result of the deposit of a mineral matrix by the osteoblasts and bone resorption is the result of the dissolution of this bone matrix by the osteoclasts. Osteoporosis is characterized by a dry loss of this bone matrix. An active mature osteoclast resorbs the bone after adhesion to the bone matrix via the secretion of proteolyptic enzymes, and protons inside the adhesion zone, leading to depressions or hollows in the surface of the bone which appear at the moment when the osteoclast detaches itself from the bone.

The compounds of formula (I) as well as their pharmaceutically acceptable addition salts have useful pharmacological properties. These compounds inhibit the bone resorption which is mediated via the osteoclasts.

The compounds of the invention are therefore useful in the treatment of diseases caused by loss of the bone matrix, in particular osteoporosis, malignant hypercalcemia, osteopenia due to bony metastases, parodontitis, hyperparathyroidism, periarticular erosions in rhumatoid arthritis, Paget's disease, osteopenia induced by immobilisation, glucocorticoid treatments or male or female sex hormone deficiencies.

They can also be used for the treatment of inflammatory, cancerous and cardiovascular disorders including arterialsclerosis and recurrence of stenosis. Finally, they can be used as inhibitors of angiogenesis and therefore in the treatment of tumours, by inhibition of their neovascularisation, diabetic retinopathies and nephropathies.

Recent studies have shown that the fixation of the osteoclast to the bone is mediated by receptors: the integrins.

Integrins are a superfamily of receptors mediating the process of cell/cell and more particularly cell/matrix adhesion, including in particular α2bβ3 as a blood platelet receptor (fibrinogen) and αvβ3 as vitronectin receptor, and bone sialoproteins such as osteopontin and thrombospondin.

These receptors which are proteinic heterodimer compounds of two subunits α and β, divalent divalent ion fixation sites such as Ca$^{2+}$ in particular and a recognition site for their ligand predefined by the nature of their subunits.

The αvβ3 receptor is a transmembrane glycoprotein which is expressed in a large number of cells including endothelial cells, smooth muscle cells, osteoclasts and cancerous cells which thus leads to a pluripotentiality of the compounds according to the invention.

The αvβ3 receptors expressed at the level of the osteoclast membrane are the basis of the adhesion/resorption process, contribute to the organisation of the cell cytoskeleton, and are involved in osteoporosis (Ross et al., J. Biol. Chem., 1987, 262, 7703).

The αvβ3 receptors expressed at the level of the smooth muscle cells of the aorta, stimulate their migration towards the neointima, which leads to the formation of arteriosclerosis and the occurence of post-angioplastic recurrence of stenosis (Brown and al, Cardiovascular Res.(1994), 28, 1815).

The endothelial cells secrete growth factors which are mitogens for the endothelium and can contribute to the formation of new blood vessels (angiogenesis). Angiogenic stimulation causes the formation of new blood vessels.

The antagonists of the αvβ3 integrin can thus lead to a regression of cancerous tumours by inducing the apoptosis of the angiogenic blood vessels. (Brook et al. Cell (1994) 79, 1157).

The natural ligands of the αvβ3 integrin contain all the RGD unit (Arg-Gly-Asp). Thepeptides containing this RGD unit as well as anti αvβ3 antibodies are known for their capacity to inhibit the resorption of dentin, preventing the adhesion of the osteoclasts on the mineralized matrices (Horton et al. Exp. Cell. Res. (1991), 195, 368).

The peptide Echistatin isolated from snake venom also containing an RGD unit is described as an inhibitor of the adhesion of osteoclasts to the bone, and is therefore a powerful inhibitor of bone resorption in tissues cultured in vitro (Sato et al. J. Cell. Biol. (1990), 111, 1713) and in vivo in the rat (Fisher et al. Endocrinology (1993), 132, 1441).

The compounds of formula (I) as well as their pharmaceutically acceptable addition salts and their esters can in particular have an affinity vis-à-vis other integrins having vitronectin (αvβ1, αvβ5, α2bβ3) for ligand by inhibiting the bond to their natural ligand.

This property thus renders the compounds of the invention of use for the prevention or the treatment of diseases the underlying pathology of which is caused by the ligands or cells which interact with the vitronectin receptor.

These compounds can also have an activity vis-à-vis other integrins which interact with their ligand via the tripeptide sequence RGD, giving them pharmacological properties which can be used for treating the pathologies associated with these receptors.

This activity vis-à-vis integrins therefore renders the compounds of the invention of use in the treatment of numerous diseases such as those mentioned above or in the article Dermot Cox DN & P 8(4) May 1995, 197–205 the content of which is integrated into the present Application.

A subject of the invention is therefore the compounds of formula (I) as medicaments, as well as their pharmaceutically acceptable addition salts or their esters.

A more particular subject of the invention is the compounds of formula (I), as well as their pharmaceutically acceptable addition salts as defined previously, as a medicament having an antagonist activity on the vitronectin receptor.

A more particular subject of invention is the compounds of formula (I), as well as their pharmaceutically acceptable addition salts as defined previously, as a medicament having an inhibitory activity on bone resorption or for the treatment or the prevention of the osteoporosis.

A quite particular subject of the invention is the compounds of formula (I), as well as their pharmaceutically acceptable addition salts as defined previously, as a medicament having an inhibitory activity on the growth of tumours or cancerous metastases.

A quite particular subject of the invention is the compounds of formula (I), as well as their pharmaceutically acceptable addition salts as defined previously, as a medicament-having an anti-inflammatory activity or for the treatment or the prevention of cardiovascular disorders, the recurrence of stenosis, arteriosclerosis, nephropathies or retinopathies.

Among the medicaments of the invention, the compounds described-in the experimental part can in particular be mentioned.

The dosage varies according to the illness to be treated and the administration route: it can vary for example from 1 mg to 1000 mg per day in adults by oral route.

The invention extends to pharmaceutical compositions containing at least one medicament as defined above as active ingredient and one or more supports, vehicles, diluents or adjuvants.

The compounds of formula (I) are used by digestive, parenteral or local route, for example by percutaneous route. They can be prescribed in the form of plain or sugar-coated tablets, gelatin capsules, granules, suppositories, pessaries, injectable preparations, sugar-coated tablets, gelatin capsules, granules, suppositories, pessaries, injectable preparations, ointments, creams, gels, microspheres, nanospheres, implants, patches, which are prepared according to the usual methods.

The active ingredient(s) can incorporated with excipients usually used in these pharmaceutical compositions, such as talc, gum arabic, lactose, starch, magnesium stearate, cocoa butter, aqueous or non aqueous vehicles, fatty substances of animal or vegetable origin, paraffin derivatives, glycols, various wetting, dispersing or emulsifying agents and preservatives.

A subject of the invention is also a process for the preparation of the compounds of formula (I) comprising the following stages:

a) a compound formula (IIa):

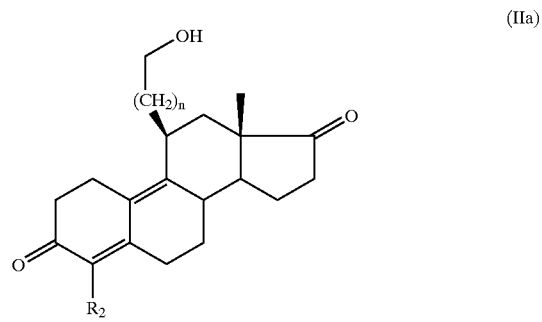

(IIa)

n being an integer varying from 1 to 6, $R_2$ being as defined previously, is firstly subjected to to the action of a halogenation reagent or a reagent activating the alcohol, then to the action of a compound of formula (F2):

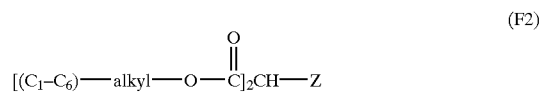

(F2)

in which Z is as defined previously, in the presence of sodium, in order to obtain the compound of formula (III):

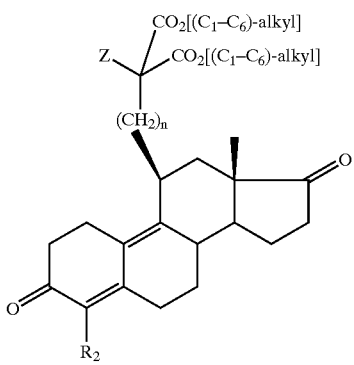

(III)

b) the compound of formula (III) is subjected to the action of a saponification agent then a decarboxylation reagent in order to obtain the compound of formula (IV):

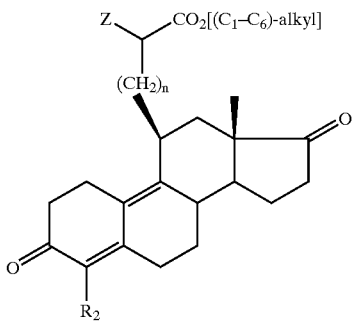

(IV)

c) the compound of formula (IV) is subjected to the action of a compound of formula (F1):

$$G-NH_2 \quad (F1)$$

in which G is as defined previously in order to obtain a compound of formula (I) which if desired or if necessary, is subjected, in an appropriate order, to one or more of the following reactions:
- action of a halogenation reagent in position 4, when $R_2$ is a hydrogen atom,
- reduction in position 17 then, if appropriate, alkylation or acylation,
- introduction of the methylene group in position 17,
- saponification,
- esterification or amidification of the acid function,
- salification by an acid or a base.

A particular subject of the invention is a process as defined previously in which the halogenation reaction in position 4, the reduction reaction in position 17 followed, if appropriate, by an alkylation or acylation as well as the introduction of the methylene group can be carried out in stages a or b, i.e. on the compounds of formula (IIa) or on the intermediate compounds of formula (III) or (IV).

A subject of the invention is also a process for the preparation of the compounds of formula (I) with Z representing a hydrogen atom comprising the following stages:

a) a compound of formula (IIb):

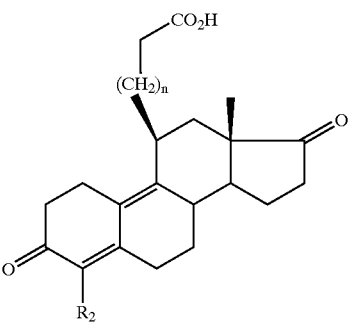

(IIb)

in which n is an integer varying from 1 to 6 and $R_2$ is a hydrogen atom is subjected to,
if appropriate, to the action of a halogenation reagent in position 4 in order to obtain the compound of formula (IIb) with R representing a halogen,
then to the action of a compound of formula (F1):

$$G-NH_2 \quad (F1)$$

in which G is as defined previously in order to obtain a compound of formula (I) which, if desired or if necessary, is subjected, in an appropriate order, to one or more of the following reactions:
- reduction in position 17 then, if appropriate, alkylation or acylation,
- introduction of the methylene group in position 17,
- esterification or amidification of the acid function,
- salification by an acid or a base.

As a variant, the reduction reactions in position 17, followed, if appropriate, by an alkylation or acylation, introduction of the methylene group in position 17, as well as esterification, amidification or salification reactions of the acid function can be carried out beforehand on the compound of formula (IIb).

The action of a halogenation reagent on the alcohol of formula (IIa) is preferably carried out by the action of carbon tetrabromide in the presence of triphenylphosphine in dichloromethane. By the action of an agent activating the alcohol, is preferably meant the preparation of a mesylate, tosylate to triflate according to the methods known to a person skilled in the art. The action of the compound of formula (F2) is carried out in particular in the presence of sodium in ethanol. The formation of a 4-halogenated derivative of the compounds of formulae (IIa) or (IIb) is carried out in particular by the action of N-bromosuccinimide ($R_2=H \rightarrow R_2=Br$) or by the action of N-chlorosuccinimide ($R_2=H \rightarrow R_2=Cl$) in the presence of a dipolar aprotic solvent such as dimethylformamide. The reduction of 17 keto to the corresponding alcohol (X=OH and Y=H) is carried out in particular by the action of an alkaline borohydride such as sodium borohydride in methanol or ethanol or by athe ction of lithium aluminium hydride.

The introduction of the methylene group in position 17 is carried out for example by the action of a wittig reagent ($Ph_3P=CH_2$) on the corresponding 17 keto compound according to the usual methods, after having protected the 3-keto function. The action of $G-NH_2$ (F1) is carried out either without solvent, or in a alcohol such as ethanol or butanol. The $G-NH_2$ amine is optionally used in the form of a salt such as the hydrochloride or hydrobromide. The decarboxylation, saponification, alkylation, acylation, esterification or acylation reactions being carried out according to the usual methods known to a person skilled in the art. The salification reactions can be carried out under the usual conditions. The process to salify the $CO_2H$ terminal group, is carried out for example in the presence of a sodium salt such as sodium carbonate or sodium or potassium acid carbonate. Similarly, the salification of the amine or the aminoguanidine which can be represented by G, by an acid, is carried out under the usual conditions. The operation is for example carried out with hydrochloric acid, for example in an ethereal solution.

The protection and deprotection reactions which are optionally necessary during the different synthesis stages are the standard methods known to a person skilled in the art. A fairly complete review can be found in the following work: Protective groups in organic synthesis T. W Greene, John Wiley & sons (1981).

By way of example, the deprotection reactions of the benzyl group can be carried out by the action of hydrogen in the presence of palladium on carbon in ethyl acetate or by the action. of trifluoroacetic acid, the deprotection reactions when P is a tertbutyldiphenylsilyl group can be carried out by the action of ammonium tetrabutyl fluoride in solution in tetrahydrofuran.

When P is a tetrahydropyrannyl group, the deprotection is carried out in the presence of an aqueous acid in an alcoholic solvent and preferably by the action of hydrochloric acid in methanol.

The compounds of formula (IIa) and (IIb) with $R_2$ representing a hydrogen atom are known and described in the European Patent Application EP-A-0384842.

The compounds of formulae (F1) and (F2) are commercially available, known or accessible to a person skilled in the art.

A subject of the invention is also the compounds of formulae (III) and (IV) as well as the compounds of formulae (IIa) and (IIb) in which $R_2$ is a halogen atom as defined above.

The following examples illustrate the invention without however limiting it.

EXAMPLE 1

Ethyl-3-[(4,5-dihydro-1H-imidazol-2-yl)hydrazono]-17-oxo-.alpha.-[[(phenylmethoxy)carbonyl]amino]-estra-4,9-diene-11-beta-hexanoate Stage A: Bromination 11-Beta-(4-bromobutyl)-estra-4,9-diene-3,17-dione 1.094 g of carbon tetrabromide and 0.865 g of triphenylphosphine are added to a solution of 1.027 g of 11-beta-(4-hydroxybutyl)-estra-4,9-diene-3,17-dione in 10 ml of dichloromethane, in several additions and agitation is carried out for one hour at approximately 26° C. After purification by chromatography 0.816 g of expected product is obtained.

IR ($CHCl_3$); C=O 1736 $cm^{-1}$, dienone 1657 and 1604 $cm^{-1}$,

Stage B: Introduction of F2=$(CO_2Et)_2$CH—$NHCO_2CH_2Ph$ diethyl [4-[3,17-dioxo-estra-4,9-diene-11-beta-yl]butyl]-[[(phenyl beta-(4-hydroxybutyl)-estra-4,9-diene-3,17-dione in 10 ml of dichloromethane, in several additions and agitation is carried out for one hour at approximately 26° C. After purification by chromatography 0.816 g of expected product is obtained.

IR ($CHCl_3$); C=O 1736 $cm^{-1}$, dienone 1657 and 1604 $cm^{-1}$,

Stage B: Introduction of F2=$(CO_2Et)_2$CH—$NHCO_2CH_2Ph$ diethyl (4-(3,17-dioxo-estra-4,9-diene-11-beta-yl]butyl]-[[(phenyl methoxy)carbonyl]amino]-propanedioate.

439 mg of the product obtained in the previous stage in 1 ml of acetonitrile and 1.5 equivalent of sodium iodide are added to a solution containing 77 mg of sodium hydride at 50% and 0.5 g of diethyl [[(phenylmethoxy)carbonyl] amino]-propanedioate in 4 ml of THF and 0.5 ml of DMF, then the reaction medium is taken to reflux for 2 hours. After purification by chromatography, 0.302 g of expected product is obtained.

IR ($CHCl_3$); =C—NH 3417 $cm^{-1}$; C=O 1756, 1736, 1721, 1656 $cm^{-1}$; C=C+aromatic+amide II 1604, 1497 $cm^{-1}$.

Stage C: Saponification/Decarboxylation Ethyl 3,17-dioxo-.alpha.-[[(phenylmethoxy)carbonyl]amino]-estra-4,9-diene-11-beta-hexanoate.

0.5 ml of 2N soda is added to a solution of 0.29 g of the product obtained in the previous stage in 5 ml of ethanol, followed by agitating for 3 hours then acidifying with 0.5 ml of 2N hydrochloric acid. 10 ml of dioxane is added, the reaction medium is taken to 100° C. for 2 hours and purified by chromatography eluting with a cyclohexane/ethyl acetate mixture 6/4. 155 mg of pure expected product is obtained.

IR ($CHCl_3$); —NH 3434 $cm^{-1}$; C=O 1735, 1722 $cm^{-1}$; dienone C=O 1657 $cm^{-1}$ C=C 1603 $cm^{-1}$, amide II+aromatic 1509 $cm^{-1}$.

Stage D: Introduction of G—$NH_2$ ethyl 3-[(4,5-dihydro-1H-imidazol-2-yl)hydrazono]-17-oxo-.alpha.-[[(phenylmethoxy)carbonyl]amino]-estra-4,9-diene-11-beta-hexanoate 0.386 g of 2-hydrazino-2-imidazoline hydrobromide is added to a solution of 0.956 g of the product obtained in the previous stage in 10 ml of ethanol, the reaction medium is taken to reflux for 3 hours and purified by chromatography eluting with a $CH_2Cl_2$/MeOH mixture 90/10. 1.06 g of crude expected product is obtained.

IR ($CHCl_3$); NH 3446 $cm^{-1}$; C=O 1734 $cm^{-1}$; C=N, C=C, amide II 1674, 1629, 1565, 1509, 1488 $cm^{-1}$.

EXAMPLE 2

3-[(4,5-Dihydro-1H-imidazol-2-yl)hydrazono]-17-oxo-.alpha.-[[(phenylmethoxy) carbonyl]amino]-estra-4,9-diene-11-beta-hexanoic Acid Method a)

1.4 ml of 2N soda is added to a solution of 0.904 g of the product obtained in Stage D of Example 1 in 5 ml of ethanol and agitation is carried out at ambient temperature for 1 hour. 1.4 ml of 2N hydrochloric acid is added, the reaction medium is purified by chromatography eluting with a $CHCl_3$/MeOH/$NH_4OH$ mixture 80/20/2 and 0.520 g of expected product is obtained in the form of a ΔE/ΔZ mixture 70/30.

Method b)

Stage A: Saponification/Decarboxylation 5 ml of 2N soda is added to a solution of 3 g of the ester obtained in Stage C of Example 1 in 60 ml of ethanol, and agitation is carried out for 1 hour at 20° C. followed by acidifying with 5 ml of 2N hydrochloric acid; 20 ml of dioxane is added, the reaction medium is taken to 120° C. for 3 hours, the solvents are evaporated off, the reaction medium is taken up in 60 ml of ethanol and 5 ml of 2N soda is added. After evaporation of the solvents, the crude product is purified by chromatography eluting with the $CHCl_3$/MeOH $NH_4OH$ mixture 8/2/0.4. 1.06 g of expected product is obtained.

Stage B: Introduction of G—$NH_2$

The operation is carried out in the same way as Example 1 Stage D starting from 266 mg of the product obtained in the previous stage and 135 mg of 2-hydrazino-2-imidazoline hydrobromide. 109 mg of expected product is obtained.

NMR (CDCl$_3$); 0.91 and 1.04 18-Me; 3.77 CH$_2$—N; 4.19 CO—CH—NH; 5.09 OCH$_2$Ph; 5.75 and 6.54 H4 35%–65% resolution (majority ΔE); 7.34 phenyl; 5.78, 6.07–6.54; 11.65–11.98 mobile H.

EXAMPLE 3

Reduction of the 17 Keto Function 3-[(4,5-Dihydro-1H-imidazol-2-yl)hydrazono]-17-hydroxy-alpha.-[[(phenylmethoxy)carbonyl]amino]-estra-4,9-diene-11-beta-hexanoic Acid A mixture constituted by 0.208 g of the product of Example 2, 14 mg of sodium borohydride and 3.5 ml of ethanol is agitated for 1 hour at ambient temperature, 3.5 ml of 1N hydrochloric acid is added, agitation is carried out for 10 minutes, the solvent is evaporated off, and the product obtained is purified by chromatographing eluting with a CHCl$_3$/MeOH/NH$_4$OH mixture 80/20/2.

0.145 g of expected product is obtained. SM: 616$^-$=[M-H]$^-$; 508$^-$=[M—OCH$_2$Ph]; 618$^+$=MH$^+$; 640$^+$=MNa$^+$.

EXAMPLE 4

3-[(Amino-iminomethyl)hydrazono]-17-oxoestra-4,9-dien-11-beta-pentanoic Acid

Stage A: Oxidation
3,17-Dioxo-estra-4,9-diene-11-beta-pentanoic Acid 7 ml of Heilbron-Jones reagent (1.89 g of CrO$_3$) is added over 22 minutes at a temperature of between 0° and −4° C. to 2.9 g of 11-beta-5-(hydroxypentyl)-estra-4,9-diene-3,17-dione in 140 ml of acetone, agitation is carried out for 5 minutes at 0° C. then 2.5 ml of methanol, 22 g of barium carbonate and 220 ml of water are added then the reaction medium is agitated vigorously for 1 hour at ambient temperature. After separation, the aqueous phase is extracted with dichloromethane, followed by washing and drying, evaporating under reduced pressure until 3.4 g of expected product is obtained.

Rf: (dichloromethane/acetone 80/20)=0.15. IR (CHCl$_3$); C=O 1736, 1709, 1657; C=C 1602 cm$^{-1}$.

Stage B—Introduction of G—NH$_2$
3-((Amino-iminomethyl)hydrazonol-17-oxoestra-4,9-dien-11-beta-pentanoic Acid A mixture constituted by 480 mg of the acid obtained in the previous stage, 285 mg of aminoguanidine hydrochloride and 10 ml of ethanol is taken to reflux for 2 hours, followed by evaporating under reduced pressure until the crude product is obtained which is purified by chromatography eluting with a CH$_2$Cl$_2$/MeOH /NH$_4$OH mixture 40/10/2 and which is then lyophilised. 170 mg of expected product is obtained in the form of a ΔZ/ΔE mixture 40/60.

NMR (DMSO 300 MHz); 0.96 18Me; 5.82(s) H4 ΔE; 6.65(s) H4 ΔZ; 6,8,7,5 broad and mobile 3H absorption.

EXAMPLE 5

3-[(Amino-iminomethyl)hydrazono]-17-oxo-estra-4,9-diene-11-beta-hexanoic Acid

The operation is carried out as in Example 4 Stage B but starting from 380 mg of 3,17-dioxo-estra-4,9-diene-11-beta-hexanoic acid and 220 mg of aminoguanidine hydrochloride in 10 ml of ethanol. 50 mg of white insoluble product corresponding to the ΔE isomer and 130 mg of beige lyophilizate corresponding to the ΔZ isomer are obtained.

NMR (ΔZ isomer) (DMSO, 300 MHz); 18 Me 1.00 (s); H4 6.73(s), mobile H's 6.89, 8.17;

NMR (ΔE isomer) (DMSO, 300 MHz); 18-Me 0.97 (s); H4 5.82(s), mobile H's 6.5 to 7.6.

EXAMPLE 6

3-[(1,4,5,6-Tetrahydro-2-pyrimidinyl)-hydrazono]-17-oxo-4,9-diene-11-beta-hexanoic Acid The operation is carried out as in Example 4 Stage B but starting from 0.597 g of 3,17-dioxo-estra-4,9-diene-11-beta-hexanoic acid and 0.453 mg of 2-hydrazono-1,4,5,6-tetrahydro-pyrimidine hydrobromide in 12.5 of ethanol. 3 fractions are isolated corresponding to different proportions of ΔE/ΔZ a) 65 mg b) 99 mg and c) 65 mg; NMR (CDCl$_{3, 300}$ MHz); Fraction b: ΔE/ΔZ mixture 90/10; 1.04(s), 1.06(s) 18-Me; 3.42(m) CH$_2$—N; 5.76(s) H4 ΔE 6.67(s)H4 ΔZ; 6.64(s) 12.40(m) mobile H's; 1.20 to 3.20(m) steroid skeleton. Fraction c: ΔE/ΔZ mixture 60/40; 1.04(s) 1.06(s) 18-Me; 3.42(m) CH$_2$N; 5.77(s) 6.66(masked) H4 6.66(s) mobile H; 1.24 to 3.05(m) steroid skeleton; 11.8(m) mobile H.

EXAMPLE 7

3-[(4,5-Dihydro-1H-imidazol-2-yl)-hydrazono]-17-oxo-estra-4,9-diene-11-beta-hexanoic Acid The operation is carried out as in Example 4 Stage B but starting from 0.5 g of 3,17-dioxo-estra-4,9-diene-11-beta-hexanoic acid, 0.353 g of 2-hydrazino-2-imidazoline hydrobromide in 12.5 ml of ethanol. 220 mg of pure expected product (ΔE/ΔZ mixture 85/15) is obtained. IR (CHCl$_3$); C=O 1733 cm$^{-1}$; C=O and/or C=N 1661 cm$^{-1}$; C=N, C=C 1617, 1597, 1546 cm$^{-1}$. NMR (DMSO, 300 MHz); 0.97(s) 18-Me; 3.40(bs) CH$_2$—N; 5.80(s)H4 ΔE; 6.60(s) H4 ΔZ; 6.53(m) 6.86(m) mobile H; 1.16 to 3.00 steroid skeleton.

EXAMPLE 8

4-Chloro-3-[(4,5-dihydro-1H-imidazol-2-yl) hydrazono]-17-oxo-estra-4,9-diene-11-beta-hexanoic Acid Stage A: 4-Chloro-3,17-dioxo-estra-4,9-diene-11-beta-hexanoic Acid 382 mg of N-chlorosuccinimide is added under a nitrogen atmosphere, at approximately 54° C., to 829 mg of 3,17-dioxo-estra-4,9-diene-11-beta-hexanoic acid in 10 ml of dimethylformamide, agitation is carried out for 10 minutes at approximately 61° C., then, after cooling down, an aqueous solution of sodium chloride is poured in, followed by extracting, washing and evaporating under reduced pressure until the crude product is obtained which is purified by chromatography eluting with a dichloromethane/acetone mixture 8/2 in order to obtain 387 mg of expected product.

IR (CHCl$_3$); C=O 1736, 1712, 1673 cm$^{-1}$; C=C 1587, 1551 cm$^{-1}$.

Stage B: Condensation
4-Chloro-3-[(4,5-dihydro-1H-imidazol-2-yl)hydrazono]-17-oxo-estra-4,9-diene-11-beta-hexanoic Acid.

159 mg of chlorinated product prepared in the previous stage and 137 mg of 2-hydrazino-2-imidazoline hydrobromide are mixed in 4 ml of ethanol. After treatment and purification, 187 mg of expected product is obtained.

IR (CHCl$_3$); =C—NH 3449 cm$^{-1}$+general absorption; C=O 1735 cm$^{-1}$; C=N+C=C+CO$_2^-$,: 1672, 1620, 1604, 1546, 1513 cm$^{-1}$.

EXAMPLE 9

3-[(Aminoiminomethyl)hydrazono]-4-chloro-17-oxo-estra-4,9-diene-11-beta-hexanoic Acid The operation is carried out as in Stage B of Example 8, starting from 380 mg of the chlorinated product prepared in Example 8 Stage A and 201 mg of aminoguanidine hydrochloride. 77 mg of expected product is obtained.

IR (Nujol); OH/NH absorption; C=O 1731 cm−1; Conjugated system+NH2 1676, 1604, 1532 cm$^{-1}$.

EXAMPLE 10

6-[3-[(4,5-Dihydro-1H-imidazol-2-yl)-hydrazono]-17-methylene-estra-4,9-diene-11-beta-yl]-2-[[(phenylmethoxy) carbonyl]amino]-hexanoic Acid Stage A: Blocking of the Alcohol with Dihydropyrane 11-beta-[4-[(tetrahydro-2H-pyran-2-yl)oxy]butyl-estra-4,9-diene-3,17-dione A solution containing 3.42 g of 11-beta-(4-hydroxybutyl)-estra-4,9-diene-3,17-one, 20 ml of ether, 9 ml of dihydropyrane and paratoluene sulphonic acid in catalytic quantity is agitated for 3 hours then 10 cm$^3$ of triethylamine is added, the solvents are evaporated off under reduced pressure and the residue is purified by chromatography eluting with a dichloromethane/acetone mixture 90/10. 3.70 g of pure expected product (Rf=0.42) is obtained.

IR (CHCl$_3$): C=O 1736, C=C 1657 cm$^{-1}$; 1603 cm$^{-1}$; NMR (CDCl$_3$); 1.08(s) 18Me; 3.08(pp) H11; 3.3 (dt) 3.73 (m) CH$_2$O; 3.51(m)–3.84(m) CH$_2$O of THP; 4.55 angular H of THP; 5.71(s) H4.

Stage B: Blocking of the Ketone in Position 3 in the Form of Methyloxime and Unblocking of the Primary OH 3-(O-methyloxime) of 11-Beta-(4-hydroxybutyl)-estra-4,9-diene-3,17-one A mixture constituted by 0.98 g of the derivative prepared in the previous stage, 0.215 g of methylhydroxylamine hydrochloride, 10 ml of methanol, 0.160 g of sodium acetate and 2 ml of water is agitated at ambient temperature for 18 hours. The reaction mixture is then diluted with 50 ml of water then extracted with dichloromethane. 0.874 g of a yellow resin is recovered which is purified by chromatography eluting with a cyclohexane/ethyl acetate mixture 7/3.

Rf: 0.17 ΔE isomer and 0.12 ΔZ isomer.

The following are recovered:

a) The Product Having an Rf of 0.17 m=0.382 g
IR (CHCl$_3$);

| | |
|---|---|
| OH | 3624 cm$^{-1}$ |
| C=O | 1734 cm$^{-1}$ 17 keto |
| C=N, C=C | 1605 cm$^{-1}$ |

NMR ΔE isomer (CDCl$_3$); 1.06(s) 18Me; 3.64(t) CH$_2$O; 2.99 H11; 3.88 (s) OMe; 5.80 (s) H4 ΔE;

b) The Product Having an Rf of 0.12 m=0.211 g
IR (CHCl$_3$);

| | |
|---|---|
| OH | 3624 cm$^{-1}$ |
| C=O | 1734 cm$^{-1}$ 17 keto |
| C=C, C=N | 1603 cm$^{-1}$ |

NMR ΔZ isomer CDCl$_3$; 1.06(s) 18Me; 3.01(bq) H11; 3.64(t) CH$_2$O; 3.87(s) OMe; 6.36(s) H4 ΔZ.

Stage C: Wittig Reaction: Introduction of the Methylene Group in Position 17 3-(O-Methyloxime) of 11-Beta-(4-hydroxybutyl)-17-methylene-estra-4,9-diene-3-one A mixture constituted by 0.635 g of triphenyl methyl phosphonium bromide and 0.199 g of potassium terbutylate is agitated under reduced pressure at 100° C. for 40 minutes. After cooling down to ambient temperature and placing under nitrogen, 5 ml of tetra-hydrofuran, and 0.162 g of the steroid prepared in the previous stage (ΔE) are introduced. The solution is taken to reflux for 3 hours then cooled down, hydrolyzed with an ammonium chloride solution and extracted. 0.480 g of a yellow resin is obtained which is purified by chromatography eluting with a cyclohexane/ethyl acetate mixture 7/3 (Rf=0.10). 0.130 g of a colourless oil is recovered.

IR (CHCl$_3$);

| | |
|---|---|
| OH | 3624 cm$^{-1}$ |
| C=C, C=N | 1654 cm$^{-1}$ |

NMR (CDCl3); 0.96(s) 18Me; 3.65(t) CH$_2$O; 3.87(s) OMe; ~4.60 CH$_2$=C; 5.77(s) H4.

Stage D: Unblocking the Ketone in Position 3 11-Beta-(4-hydroxybutyl)-17-methylene-estra-4,9-dien-3-one A solution containing 0.188 g of product prepared in the previous stage, 2 ml of acetone and 0.5 ml of 6N hydrochloric acid is agitated at ambient temperature for 24 hours. The reaction medium is diluted with water then extracted with dichloromethane. 0.174 g of a resin is obtained which is purified by chromatography eluting with a cyclohexane/ethyl acetate mixture 7–3. A pure yellow resin is recovered m=0.076 g. (Rf=0.10) IR (CHCl$_3$);

| | |
|---|---|
| OH | 3625 cm$^{-1}$ |
| C=O | 1654 cm$^{-1}$ |
| C=C | 1603 cm$^{-1}$ |

Stage E: Bromination then Condensation of the Chain Diethyl [4-(17-methylene-3-oxo-estra-4,9-dien-11-beta-yl) butyl][[(phenylmethoxy)carbonyl]amino]propanedioate 0.543 g of triphenylphosphine is added in small fractions to a solution containing 0.470 g of steroid prepared in the previous stage, 5 ml of dichloromethane and 0.685 g of carbon tetrabromide, the solution is agitated for 30 minutes, concentrated to dryness then purified by filtration on silica. 0.340 g of a yellow resin is obtained which corresponds to the brominated derivative.

A solution of 0.640 g of diethyl [[(phenylmethoxy)carbonyl]amino]-propanedioate in solution in 1 cm$^3$ of THF is introduced slowly into a suspension of sodium hydride at 50% in oil (0.1 g) in 0.5 ml of DMF and 2.5 ml of anhydrous THF. After 30 minutes, the brominated derivative obtained above in solution in 1 ml of THF is introduced. 0.310 g of sodium iodide and 1 ml of acetonitrile are then added, and the reaction medium is taken to reflux for 3 hours. The reaction mixture is hydrolysed with an ice-cooled monosodium phosphate solution then extracted with dichloromethane. 1.2 g of a yellow resin is obtained which is purified by chromatography on silica eluting with a dichloromethane/acetone mixture 97/3. 0.164 g of a yellow-oil is recovered.

IR (CDCl$_3$); Little or no OH;

| | |
|---|---|
| NH | 3418 cm$^{-1}$ |
| C=O | 1756 sh, 1736 max, 1724 sh, 1654 conjugated ketone |
| C=C | 1603 max |
| And | 1589 sh |
| Amide II | 1498 |

Stage F: Saponification, Decarboxylation then Formation of the Iminoguanidine Ethyl 6-[3-[(4,5-dihydro-1H-imidazol-2-yl)hydrazonol-17-methylene-estra-4,9-dien-11-beta-yl]-2-[[(phenylmethoxy) carbonyl]amino]-hexanoate.

a) Saponification-Decarboxylation

A solution containing 0.148 g of the derivative prepared in the previous stage, 3 ml of ethanol and 0.23 ml of 2N soda is agitated at ambient temperature for one hour, then acidified with 0.23 ml of 2N hydrochloric acid, followed by agitating for 10 minutes and concentrating to dryness. Rf=0.52 eluent dichloromethane/methanol/ammonia 80/20/4 b) Formation of the Iminoguanidine: Introduction of G—NH$_2$

The crude product obtained above is taken up in 3 ml of isopropanol in the presence of 0.1 g of 2-imidazolidinone hydrazone and a catalytic quantity of paratoluene sulphonic acid. The reaction medium is taken to reflux for 1 hour then concentrated to dryness and purified by chromatography eluent (dichloromethane/methanol/ammonia 80–20–4). 0.089 g of expected product is recovered.

IR (CHCl3); NH 3446 cm$^{-1}$, absence of dienone.

Stage G: Saponification of the Ethyl Ester-6[3-[(4,5-dihydro-1H-imidazol-2-yl)hydrazono]-17-methylene-estra-4,9-diene-11-beta-yl]-2-[[(phenylmethoxy)-carbonyl]amino]-hexanoic Acid A solution containing 86 mg of the ethyl ester prepared in the previous stage, 2 ml of ethanol and 0.3 ml of 2N soda is agitated at ambient temperature for one hour. The solution is neutralized by the addition of 0.3 ml of 1N hydrochloric acid, followed by agitating for 20 minutes then concentrating to dryness. The crude product obtained is purified by chromatography on silica eluting with a dichloromethane/methanol/ammonia mixture 80/20/2. 47 mg of expected product is obtained.

M.S.: Molecular weight structure 613. 614$^+$=[M+H]$^+$ 612$^-$=[M−H]$^-$ 636$^+$=[M+Na]$^+$ Pharmaceutical Compositions Tablets corresponding to the following formula:

product of Example 2 50 mg excipient (talc, starch, magnesium stearate)

QS for a tablet completed at 120 mg

Pharmacological Study of the Products of the Invention

1—Study by the Products of the Invention of the Bond Displacement: Vitronectin/Vitronectin Receptor ($\alpha v\beta_3$) Protocol 96 well MaxiSorp plates are coated overnight at 4° C., with 100 μl of human vitronectin (cf Yatohgo et al. Cell., Structure and fraction 13: 281–292 (1988) at 2 μg/ml, (dilution in coating buffer).

The following day, the wells are emptied and the ligands (vitronectin) are then fixed (see fixation buffer) for 1 hour at ambient temperature under gentle agitation. The wells are washed six times (see washing buffer), then per well and in this order the following are added:

40 μl of incubation buffer,

10 μl of the diluted product to be tested, (the products are diluted in a 50/50 mixture of DMSO-H$_2$O)

20 μl of $\alpha v\beta_3$ human receptor (cf Pytela et al. Methods Enzymol (1987) 144:475) (dilution in incubation buffer, to be adapted according to the batch of receptor and according to the ligand).

The ligand, the $\alpha v\beta_3$ human receptor and the products to be studied are incubated for 3 hours at ambient temperature under gentle agitation.

The wells are again washed six times, then incubated for 2 hours at ambient temperature under gentle agitation, in the presence of 100 μl of 4B12-HRP antibody, anti-receptor coupled to a peroxydase (the 4B12-HRP antibody is diluted in incubation buffer. The dilution is to be adapted according to the batch of receptor).

The wells are then washed six times before measurement of the ligand-receptor bond done by the intermediate of a peroxydase visualizing kit (TMP Microwell Peroxydase Substrate System Kirkegaard: Ref. cat. 50-76-00). This kit contains a flask A of substrate (3,3',5,5'-tetramethylbenzidine at 0.4 g/l) and a flask B (H2O2 at 0.02% in Citrate/Citric acid buffer). Extemporaneously, a volume of A is mixed with a volume of B, then the reaction mixture is distributed at a rate of 100 μl/wells. The enzymatic reaction develops in 12' for Vitronectin/$\alpha v\beta_3$, and then its evolution is stopped by the addition of 100 μl of 1M phosphoric acid.

The optical density is measured at 450 nm.

Buffers:

coating buffer: 0.05 M carbonate, NaOH pH 9.6 fixation buffer: PBS containing 0.5% of BSA (pH 7.4)

washing buffer: PBS containing 0.05% of Tween 20 (pH 7.4)

incubation buffer:

50 mM TRIS pH 7.4

0.5% BSA 1 mM MnCl$_2$

50 AM CaCl$_2$

50 AM MgCl$_2$ 100 mM NaCl$_1$

Expression of the Results:

the following curve is drawn: the bonding percentage of human vitronectin as a function of the logarithm of the concentration of each product tested. For each product the IC$_{50}$ is determined according to the following formula:

$$IC_{50}=(BO+Bmin)/2$$

BO=Maximum bond in the absence of any product

Bmin=Minimum bond in the presence of the highest concentration of the product.

RESULTS:

| Examples | Competition binding test Vn/VnR (($\alpha_v\beta_3$) IC$_{50}$ in μM |
|---|---|
| 4 | 0.133 |
| 5a ΔE | 0.054 |
| 5b ΔZ | 0.375 |
| 9 | 1.95 |
| 8 | 0.017 |
| 7 | 0.025 |
| 6b 60/40 | 0.038 |

-continued

| Examples | Competition binding test Vn/VnR (($\alpha_v\beta_3$) IC$_{50}$ in $\mu$M |
|---|---|
| 6a 90/10 | 0.020 |
| 2 | 0.030 |
| 3 | 0.070 |

What is claimed is:
1. A compound of the formula

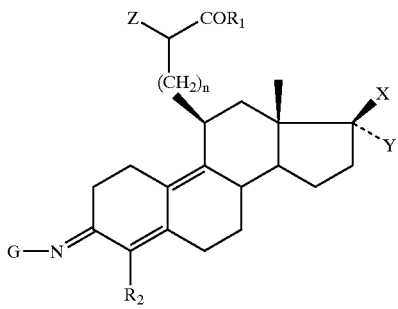

wherein X and Y form together with the carbon which carries them C=O or C=CH$_2$ or X is selected from the group consisting of hydroxy, alkoxy of 1 to 6 carbon atoms, alkylcarbonyloxy of 2 to 6 carbon atoms and Y is hydrogen;
R$_1$ is selected from the group consisting of hydroxy, alkoxy of 1 to 6 carbon atoms, amino, alkylamino of 1 to 6 carbon atoms;
R$_2$ is hydrogen or halogen;
Z is selected from the group consisting of hydrogen, —NHSO$_2$Ra, —NHCORa, —NHCO$_2$Ra, NHSO$_2$NHRa and —NHCONHRa;
G is selected from the group consisting of

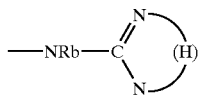

(G1) in which (H) forms with the —N=C—NH— unit the remainder of a heterocycle,
(G2) which is

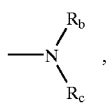

a heterocycle (G3),
—NRb—C(=A)—NHRc (G4) in which A is sulfur or oxygen or NH, and —NRb—SO$_2$Rc (G5),
Ra, Rb and Rc are individually selected from the group consisting of hydrogen, —(CH$_2$)$_m$-Alk, —(CH$_2$)$_m$-Ar and —(CH$_2$)$_m$-Het or Rb and Rc together with the nitrogen atom to which they are linked form a heterocycle,
Alk is alkyl or cycloalkyl, saturated or unsaturated, unaromatic hydrocarbon of up to 12 carbon atoms, substituted by R$_3$ or unsubstituted, Ar is carbocyclic aryl substituted by R$_3$ or unsubstituted and Het is aromatic or nonaromatic heterocycle substituted by R$_3$ or unsubstituted, n is an integer from 1 to 6, m is 0, 1, 2 or 3,
R$_3$ is selected from the group consisting of
a) halogen, oxo, cyano, nitro, formyl, carboxy, alkoxyoxycarbonyl of 2 to 6 carbon atoms and carboxyamide,
b) alkyl, alkenyl and alkynyl of up to 6 carbon atoms, unsubstituted or substituted by at least one halogen,
c) cycloalkyl of 3 to 12 carbon atoms, alkoxy and alkylthio of 1 to 6 carbon atoms,
d) amino, alkylamino of 1 to 6 carbon atoms, dialkylamino of 2 to 12 carbon atoms optionally in oxidized form,
aminoalkyl of 1 to 6 carbon atoms or dialkylaminoalkyl of 3 to 8 carbon atoms,
dialkylaminoalkoxy of 3 to 18 carbon atoms,
e) an optionally acylated hydroxy of 1 to 12 carbon atoms, an acyl of 1 to 12 carbon atoms unsubstituted or substituted by chlorine, iodine or fluorine,
f) aryl, carbocyclic or heterocyclic, aralkyl or aryloxy unsubstituted or substituted by at least one substituent mentioned above,
said compounds of Formula I being in all their possible isomer forms, isolated or in a mixture, or their esters and their addition salts with pharmaceutically acceptable acids and bases.
2. A compound of claim 1 wherein R$_1$ is hydroxyl and G is —NH—C(=NH)—NHR$_c$ or their pharmaceutically acceptable addition salts.
3. A compound of claim 1 wherein R$_1$ is hydroxyl and G is selected from the group consisting of:

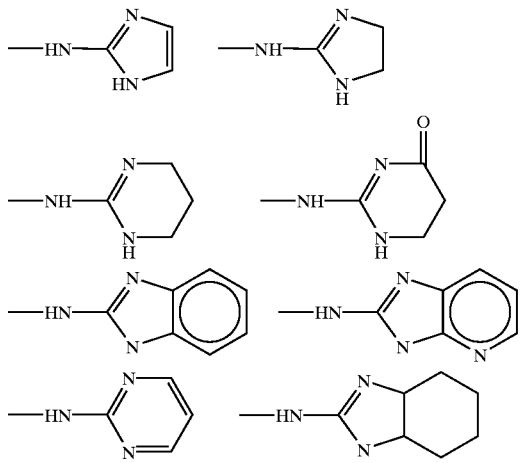

or their pharmaceutically acceptable addition salts.
4. A compound of claim 1 wherein Z is selected from the group consisting of hydrogen, —NHCO$_2$CH$_2$Ph, —NHAc and —NHCO$_2$CH$_3$ and G is selected from the group consisting of

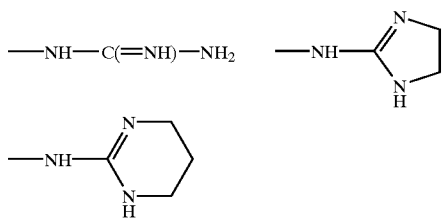

or their pharmaceutically acceptable addition salts.

5. A compound of claim 1 selected from the group consisting of:

ethyl-3-[(4,5-dihydro-1H-imidazol-2-yl)hydrazono]-17-oxo-alpha.-[[phenylmethoxy)carbonyl]amino]-estra-4,9-diene-11-beta-hexanoate, 3-[(4,5-dihydro-1H-imidazol-2-yl)hydrazono]17-oxo-.alpha.-[[phenylmethoxy)carbonyl]amino]-estra-4,9-diene-11-beta-hexanoic acid, 3-(4,5-dihydro-1H-imidazol-2-yl)hydrazono]-17-hydroxy.alpha.-[[(phenylmethoxy) carbonyl]amino]-estra-4,9-diene-11-beta-hexanoic acid, 3-[(aminoiminomethyl)hydrazono]-17-oxoestra-4,9-dien-11-beta-pentanoic acid, 3-[(1,4,5,6-tetrahydro-2-pyrimidinyl)hydrazoo]-17-oxo-4,9-diene-11-beta-hexanoic acid, 3-[(4,5-dihydro-1H-imidazol-2-yl)hydrazono]-17-oxo-estra-4,9-diene-11-beta-hexanoic acid, 4-chloro-3-[(4,5-dihydro-1H-imidazol-2-yl)hydrazono]-17-oxoestra-4,9-diene-11-beta-hexanoic acid, 3-[(aminoiminomethyl)hydrazono]-4-chloro-17-oxo-estra-4,9-diene-11-beta-hexanoic acid, and 3-[(aminoiminomethyl)hydrazono]-17-oxoestra-4,9-diene-11-beta-hexanoic acid.

6. A process for the preparation of a compound of claim 1 comprising:

a) subjecting a compound of formula

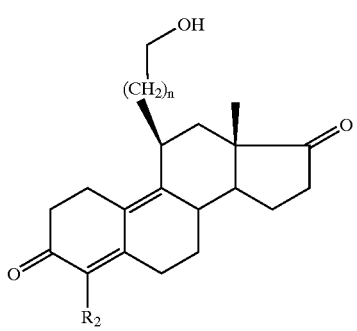

IIa wherein n is an integer from 1 to 6, $R_2$ is defined as in claim 1, first, to the action of a halogenation reagent or of an activation reagent of the alcohol, then to the action of a compound of formula F2 in the presence of sodium:

$(CO_2Alk)_2CH—Z$     F2 wherein Alk is alkyl of 1 to 6 carbon atoms and Z is as defined in claim 1 to obtain a compound of formula

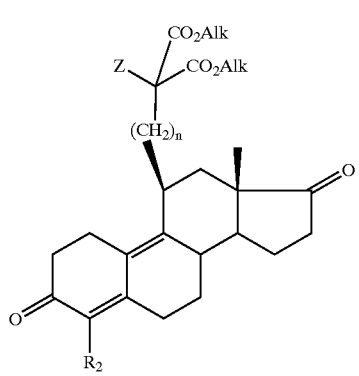

III b) subjecting the compound of formula III to the action of a saponification, then a decarboxylation reagent to obtain the compound of the formula

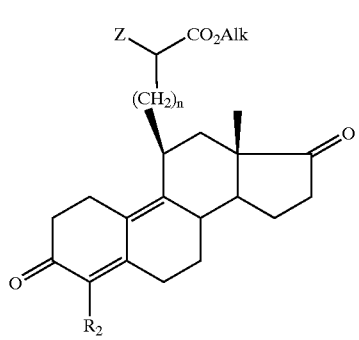

IV c) subjecting the compound of formula IV to the action of a compound of the formula

G—NH$_2$     F1 wherein G is as defined in claim 1 to obtain a compound of formula I which optionally or if necessary, is subjected in an appropriate order, to one or more of the following reaction:

action of a halogenation reagent in position 4 when $R_2$ is hydrogen, reduction in position 17 then, optionally alkylation, saponification, esterification or amidification of the acid function and salification by an acid or by a base.

7. The process of claim 6 wherein the halogenation reaction in position 4, the reduction reaction in position 17 can be carried out on the compounds of formula IIa or on the intermediate compounds of formula III or IV.

8. A process for the preparation of a compound of claim 1 where Z is a hydrogen comprising a) reacting a compound of the formula:

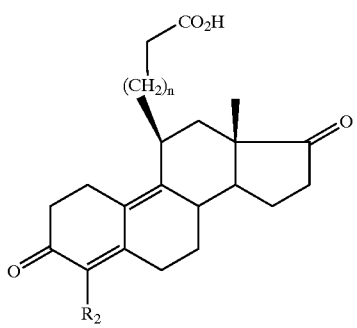

wherein n is an integer from 1 to 6 and $R_2$ is hydrogen, if appropriate to the action of a halogenation reagent in position 4 to obtain the compound of formula IIb with $R_2$ being halogen,
then to the action of a compound of the formula

   F1 in which G is as defined in claim 1 to obtain a compound of formula I which optionally or if necessary, is subjected, in an appropriate order, to one or more of the following reactions:
reduction in position 17 then, optionally, alkylation or acylation,
introduction of methylene in position 17,
esterification or amidification of the acid function,
salification by an acid or a base.

9. The process of claim 8 wherein the reduction in position 17, optionally, followed by alkylation or acylation,
introduction of methylene in position 17, and
the esterification, amidification or salification reactions of the acid function can be carried out first on the compound of formula IIb.

10. Pharmaceutical compositions containing one or more medicaments according to claim 1 and one or more supports, vehicles, diluents or adjuvants.

11. A method of treating bone disease caused by loss of bone matrix in warm-blooded animals comprising administering to warm-blooded animals in need thereof an amount of a compound of claim 1 sufficient to prevent loss of bone matrix.

12. The method of claim 11 wherein the disease is selected from the group consisting of osteoporosis, malignant hypercalcemia, osteopenia due to bony metastases, parodontitis, hyper-parathyrodism, periarticular erosions in rheumatoid arthritis, Paget's disease, osteopenia induced by immobilization, glucocorticoid treatments or male or female sex hormone deficiencies.

* * * * *